(12) United States Patent
Lipowicz

(10) Patent No.: US 10,721,965 B2
(45) Date of Patent: Jul. 28, 2020

(54) E-VAPOR DEVICE INCLUDING HEATER STRUCTURE WITH RECESSED SHELL LAYER

(71) Applicant: Altria Client Services LLC, Richmond, VA (US)

(72) Inventor: Peter Lipowicz, Midlothian, VA (US)

(73) Assignee: Altria Client Services LLC, Richmond, VA (US)

( * ) Notice: Subject to any disclaimer, the term of this patent is extended or adjusted under 35 U.S.C. 154(b) by 682 days.

(21) Appl. No.: 15/208,969

(22) Filed: Jul. 13, 2016

(65) Prior Publication Data

US 2017/0027227 A1 Feb. 2, 2017

Related U.S. Application Data

(60) Provisional application No. 62/198,365, filed on Jul. 29, 2015.

(51) Int. Cl.
*A24F 47/00* (2020.01)
*A61M 11/04* (2006.01)
(Continued)

(52) U.S. Cl.
CPC ......... *A24F 47/008* (2013.01); *A61M 11/042* (2014.02); *A61M 15/06* (2013.01);
(Continued)

(58) Field of Classification Search
CPC .. A61M 2205/3653; A61M 2205/8203; A61M 11/042; A61M 15/06;
(Continued)

(56) References Cited

U.S. PATENT DOCUMENTS

| 5,224,498 A | 7/1993 | Deevi et al. |
| 5,573,692 A | 11/1996 | Das et al. |

(Continued)

FOREIGN PATENT DOCUMENTS

| CN | 203314107 U | 12/2013 |
| CN | 203986095 U | 12/2014 |

(Continued)

OTHER PUBLICATIONS

International Search Report and Written Opinion issued in International Application No. PCT/EP2016/068089, dated Oct. 19, 2016.

(Continued)

*Primary Examiner* — Shawntina T Fuqua
(74) *Attorney, Agent, or Firm* — Harness, Dickey & Pierce, P.L.C.

(57) ABSTRACT

An e-vapor device may include a pre-vapor sector and a heater structure arranged in thermal contact with the pre-vapor sector. The pre-vapor sector is configured to hold and dispense a pre-vapor formulation. The heater structure includes a base wire and a shell layer coating the base wire. The base wire is insulated from the shell layer. The shell layer includes at least one recessed portion between a first unrecessed portion and a second unrecessed portion. The at least one recessed portion is a thinner section of the shell layer that is configured to vaporize the pre-vapor formulation to generate a vapor. As a result of the heater design, the heater structure is stiffer and more robust than other related heaters in the art, thus allowing more options for its implementation.

19 Claims, 10 Drawing Sheets

(51) Int. Cl.
*A61M 15/06* (2006.01)
*H05B 1/02* (2006.01)
*H05B 3/40* (2006.01)

(52) U.S. Cl.
CPC ............ *H05B 1/0297* (2013.01); *H05B 3/40* (2013.01); *A61M 2205/3653* (2013.01); *A61M 2205/8206* (2013.01)

(58) Field of Classification Search
CPC ... A24F 47/008; A24F 47/004; H05B 1/0297; H05B 3/40; H05B 3/84; H05B 3/141; H05B 3/46; H05B 3/34; H05B 2203/017; H05B 2203/002; H05B 2203/003; H05B 2203/004; H05B 2203/005; H05B 2203/031; H05B 2203/021; H05B 2214/02
See application file for complete search history.

(56) References Cited

U.S. PATENT DOCUMENTS

| | | | |
|---|---|---|---|
| 5,878,752 | A | 3/1999 | Adams et al. |
| 5,944,025 | A | 8/1999 | Cook et al. |
| 8,997,753 | B2 | 4/2015 | Li et al. |
| 9,352,288 | B2 | 5/2016 | Terry et al. |
| 2011/0155153 | A1* | 6/2011 | Thorens ............... H05B 3/58 131/329 |
| 2013/0192615 | A1 | 8/2013 | Tucker et al. |
| 2013/0220316 | A1 | 8/2013 | Oglesby et al. |
| 2014/0060554 | A1 | 3/2014 | Collett et al. |
| 2014/0109905 | A1 | 4/2014 | Yamada et al. |
| 2014/0130816 | A1* | 5/2014 | Liu ..................... A24F 47/008 131/329 |
| 2014/0150783 | A1 | 6/2014 | Liu |
| 2014/0182608 | A1 | 7/2014 | Egoyants et al. |
| 2014/0186015 | A1 | 7/2014 | Breiwa, III. et al. |
| 2014/0187972 | A1 | 7/2014 | Burkett |
| 2015/0027471 | A1 | 1/2015 | Feldman et al. |
| 2015/0181934 | A1 | 7/2015 | Lyubomirskiy et al. |
| 2016/0143361 | A1 | 5/2016 | Juster et al. |

FOREIGN PATENT DOCUMENTS

| | | |
|---|---|---|
| CN | 104770895 A | 7/2015 |
| DE | 3832342 C1 | 7/1989 |
| EA | 201100197 A1 | 3/2012 |
| EA | 019736 B1 | 5/2014 |
| GB | 833784 A | 4/1960 |
| JP | 2014216287 * | 11/2014 |
| JP | 2014216287 A | 11/2014 |
| RU | 138386 U1 | 3/2014 |
| WO | WO-98/16088 A1 | 4/1998 |
| WO | WO-2012/033421 A1 | 3/2012 |
| WO | WO-2013/098411 A1 | 7/2013 |

OTHER PUBLICATIONS

Office Action for corresponding U.S. Appl. No. 15/166,450, dated Jan. 16, 2018.
Office Action for corresponding U.S. Appl. No. 15/166,450, dated Aug. 27, 2018.
Office Action for corresponding U.S. Appl. No. 15/166,450, dated Jun. 3, 2019.
Office Action for corresponding Russian Application No. 2017145592, dated Dec. 17, 2019.
U.S. Office Action dated Dec. 4, 2019 for correspnding U.S. Appl. No. 15/166,450.
Russian Notice of Allowance dated Apr. 15, 2020 for corresponding Russian Application No. 2017145592/03(078057).
Chinese Office Action and Search Report dated Mar. 18, 2020 for corresponding Chinese Application No. 201680040137.7.

* cited by examiner

E-VAPOR DEVICE INCLUDING HEATER STRUCTURE WITH RECESSED SHELL LAYER

CROSS-REFERENCE TO RELATED APPLICATION

The present application claims priority under 35 U.S.C. § 119 to U.S. Provisional Application No. 62/198,365, filed Jul. 29, 2015, the entire contents of which is hereby incorporated herein by reference.

BACKGROUND

Field

The present disclosure relates to e-vapor devices and heater structures for such devices.

Description of Related Art

Electronic vapor devices are electrically-powered articles configured to vaporize a pre-vapor formulation for the purpose of producing a vapor that is drawn through an outlet of the device when a negative pressure is applied. Electronic vapor devices may also be referred to as e-vapor devices or e-vaping devices. An e-vapor device includes a reservoir configured to hold the pre-vapor formulation, a wick that is arranged in communication with the pre-vapor formulation, a heating element that is arranged in thermal proximity to the wick, and a power source configured to supply electricity to the heating element. The heating element may be in a form of a relatively thin wire that is coiled a plurality of times around the wick. Accordingly, when a current is supplied to the heating element during the operation of the e-vapor device, the wire undergoes resistive heating to vaporize the pre-vapor formulation in the wick to produce a vapor that is drawn through an outlet of the device when a negative pressure is applied.

SUMMARY

An e-vapor device may include a pre-vapor sector and a heater structure arranged in thermal contact with the pre-vapor sector. The pre-vapor sector is configured to hold and dispense a pre-vapor formulation. The heater structure includes a base wire and a shell layer coating the base wire. The base wire is insulated from the shell layer. The shell layer may include at least one recessed portion between a first unrecessed portion and a second unrecessed portion. The at least one recessed portion is a thinner section of the shell layer that is configured to vaporize the pre-vapor formulation to generate a vapor.

The pre-vapor sector may include a reservoir and a dispensing interface. The at least one recessed portion of the shell layer may be arranged to press against the dispensing interface of the pre-vapor sector. The heater structure may have a yield strength ranging from 50 to 600 MPa.

The base wire of the heater structure may be an anodized wire. The anodized wire may be an object wire coated with an anodic layer. The object wire may be an aluminum wire, a titanium wire, a zinc wire, a magnesium wire, a niobium wire, a zirconium wire, a hafnium wire, or a tantalum wire. The anodic layer may have a dielectric strength of at least 150 V. The anodic layer may have a thickness ranging from 500 to 10,000 nm.

Alternatively, the base wire may be a transition metal-based wire coated with vitreous enamel. The transition metal-based wire may be a nickel wire, a nickel-chromium wire, or a stainless steel wire.

The first unrecessed portion is separated from the second unrecessed portion by the at least one recessed portion of the shell layer. The at least one recessed portion may be configured to reach a temperature that is at least double a temperature of the first and second unrecessed portions when a current flows through the shell layer. A thickness of the at least one recessed portion of the shell layer may range from 0.01 to 1 μm. A thickness of the first and second unrecessed portions of the shell layer may range from 10 to 100 μm. The first and second unrecessed portions of the shell layer are connected to opposite terminals of a power source. The at least one recessed portion of the shell layer has a resistivity ranging from 0.02 to 0.2 μΩ·m. The shell layer may be formed of platinum or gold.

The at least one recessed portion may be in a form of a first recessed portion and a second recessed portion. The first and second recessed portions may be between opposite sides of the first and second unrecessed portions. The first and second recessed portions coil around the base wire.

A method of generating a vapor for an e-vapor device may include thermally contacting a pre-vapor sector within the e-vapor device with a heater structure. The heater structure may include a base wire and a shell layer coating the base wire. The base wire is insulated from the shell layer. The shell layer may include at least one recessed portion between a first unrecessed portion and a second unrecessed portion. The thermally contacting may include heating a pre-vapor formulation of the pre-vapor sector with the at least one recessed portion of the shell layer to generate the vapor.

BRIEF DESCRIPTION OF THE DRAWINGS

The various features and advantages of the non-limiting embodiments herein may become more apparent upon review of the detailed description in conjunction with the accompanying drawings. The accompanying drawings are merely provided for illustrative purposes and should not be interpreted to limit the scope of the claims. The accompanying drawings are not to be considered as drawn to scale unless explicitly noted. For purposes of clarity, various dimensions of the drawings may have been exaggerated.

DETAILED DESCRIPTION

Figure 1A:
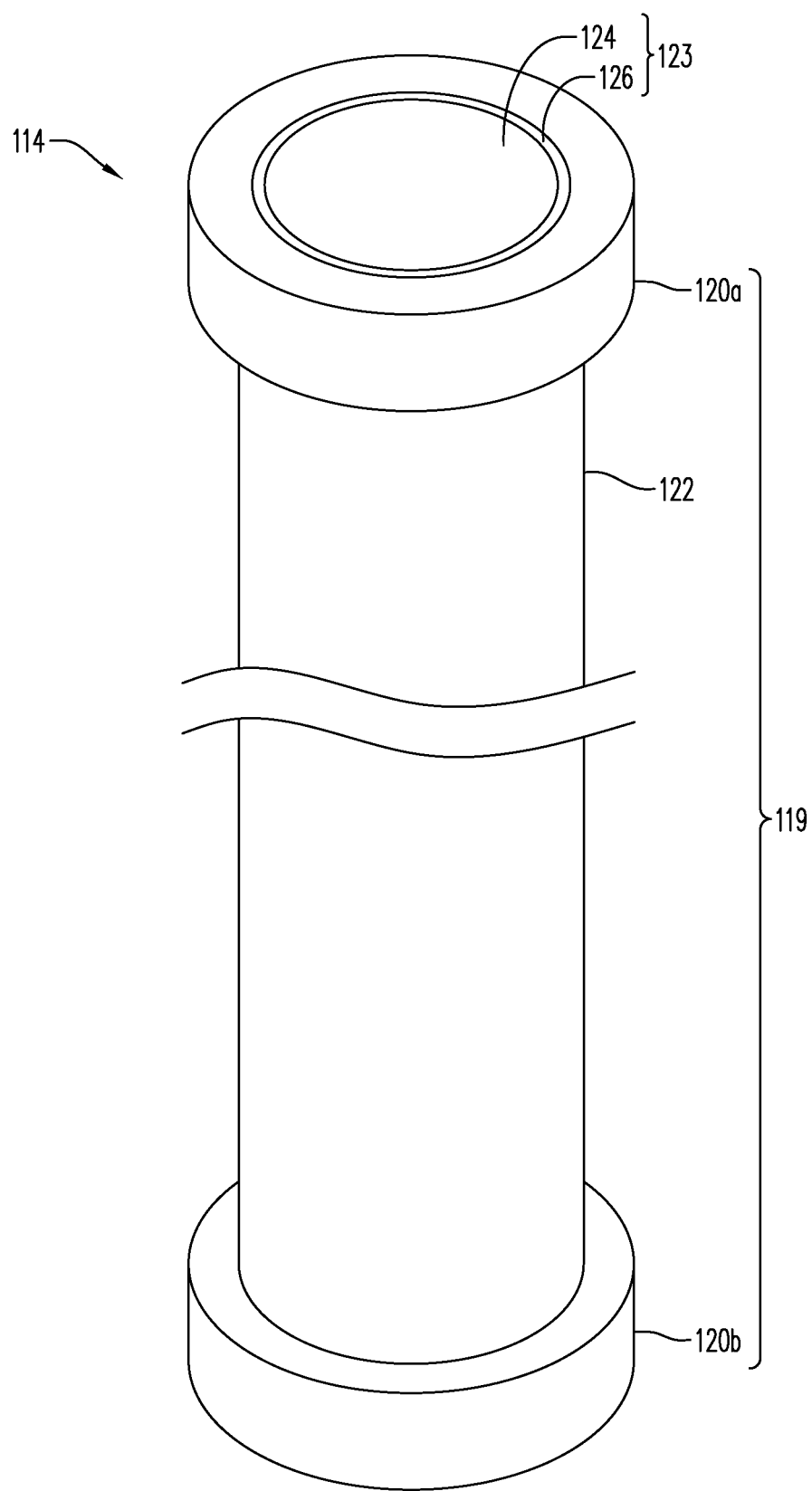
FIG. 1A is a partial, perspective view of a heater structure having a shell layer with a recessed portion according to an example embodiment.

It should be understood that when an element or layer is referred to as being "on," "connected to," "coupled to," or "covering" another element or layer, it may be directly on, connected to, coupled to, or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It should be understood that, although the terms first, second, third, etc. may be used herein to describe various elements, components, regions, layers and/or sections, these elements, components, regions, layers, and/or sections should not be limited by these terms. These terms are only used to distinguish one element, component, region, layer, or section from another region, layer, or section. Thus, a first element, component, region, layer, or section discussed below could be termed a second element, component, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

FIG. 1A is a partial, perspective view of a heater structure having a shell layer with a recessed portion according to an example embodiment. Referring to FIG. 1A, the heater structure 114 is a compound arrangement in that the heater structure 114 is composed of at least two different constituent parts. As a result of the heater design, the heater structure 114 is stiffer and more robust than other related heaters in the art, thus allowing more options for its implementation. Additionally, because FIG. 1A is only a partial view of the heater structure 114, it should be understood that the heater structure 114 may have various lengths and forms when implemented for its intended purpose.

The heater structure 114 may be utilized in an e-vapor device. In particular, the heater structure 114 may be arranged so as to be in thermal contact with a pre-vapor sector of the e-vapor device, wherein the pre-vapor sector is configured to hold and dispense a pre-vapor formulation. A pre-vapor formulation is a material or combination of materials that may be transformed into a vapor. For example, the pre-vapor formulation may be a liquid, solid, and/or gel formulation including, but not limited to, water, beads, solvents, active ingredients, ethanol, plant extracts, natural or artificial flavors, and/or vapor formers such as glycerine and propylene glycol. In an example embodiment, the pre-vapor formulation may be an e-liquid that is held and dispensed by a liquid sector. During the operation of the e-vapor device, the heater structure 114 is configured to vaporize the pre-vapor formulation to generate a vapor that is drawn through an outlet of the device (e.g., in response to the application of a negative pressure).

As shown in FIG. 1A, the heater structure 114 includes a base wire 123 and a shell layer 119 coating the base wire 123. The shell layer 119 is formed of a material that is relatively non-reactive and capable of undergoing resistive heating to vaporize a pre-vapor formulation. For instance, the shell layer 119 may be formed of platinum (Pt) or gold (Au), although example embodiments are not limited thereto. The base wire 123 is insulated from the shell layer 119. The shell layer 119 includes a recessed portion 122 between a first unrecessed portion 120*a* and a second unrecessed portion 120*b*. In an example embodiment, the first unrecessed portion 120*a* is separated from the second unrecessed portion 120*b* by the recessed portion 122 of the shell layer 119. The recessed portion 122 is a thinner section of the shell layer 119 that is configured to vaporize the pre-vapor formulation to generate a vapor. The thickness of the recessed portion 122 of the shell layer 119 may range from 0.01 to 1 μm, while the thickness of the first unrecessed portion 120*a* and the second unrecessed portion 120*b* of the shell layer 119 may range from 10 to 100 μm. The shell layer 119 may be deposited via sputtering, and the recessed portion 122 can be formed with a mask pattern, although example embodiments are not limited thereto.

To operate the heater structure 114, the first unrecessed portion 120*a* and the second unrecessed portion 120*b* of the shell layer 119 are connected to opposite terminals of a power source (e.g., battery). For instance, the first unrecessed portion 120*a* of the shell layer 119 may be connected to a positive terminal of a power source, while the second unrecessed portion 120b of the shell layer 119 may be connected to a negative terminal of the power source. Conversely, the first unrecessed portion 120a of the shell layer 119 may be connected to a negative terminal of a power source, while the second unrecessed portion 120b of the shell layer 119 may be connected to a positive terminal of the power source.

When a current is supplied to the shell layer 119, heat is generated (as a result of the passage of the current therethrough) by Joule heating, which is also referred to in the art as ohmic heating or resistive heating. In particular, an electric current passing through the shell layer 119 encounters resistance, which is the opposition to the passage of the electric current therethrough, thus resulting in the heating of the shell layer 119, particularly at the recessed portion 122. For instance, the recessed portion 122 may be configured to reach a temperature that is at least double a temperature of the first unrecessed portion 120a and the second unrecessed portion 120b when a current flows through the shell layer 119, although example embodiments are not limited thereto.

The resistance of a given object depends primarily on the material and the shape of the object. For a given material, the resistance is inversely proportional to the cross-sectional area. For instance, a thick wire of a particular metal will have a lower resistance than a thin wire of that same metal. Additionally, for a given material, the resistance is proportional to the length. Consequently, a short wire of a particular metal will have a lower resistance than a long wire of that same metal.

The resistance R of a conductor of uniform cross section can be expressed as $$R = \rho \frac{L}{A},$$

where ρ is the resistivity (Ω·m), L is the length of the conductor (m), and A is the cross-sectional area of the conductor (m²). The above equation may also be rearranged and expressed in terms of resistivity ρ, wherein $$\rho = \frac{RA}{L}.$$

Resistivity ρ is a measure of a given material's ability to oppose the flow of electric current and varies with temperature. Resistivity ρ is an intrinsic property, unlike resistance R. In particular, the wires of a given material (irrespective of their shape and size) will have approximately the same resistivity, but a long, thin wire of the given material will have a much larger resistance than a thick, short wire of that same material. Every material has its own characteristic resistivity. Thus, the resistivity of a wire at a given temperature depends only on the material used to form the wire and not on the geometry of the wire.

Figure 1B:
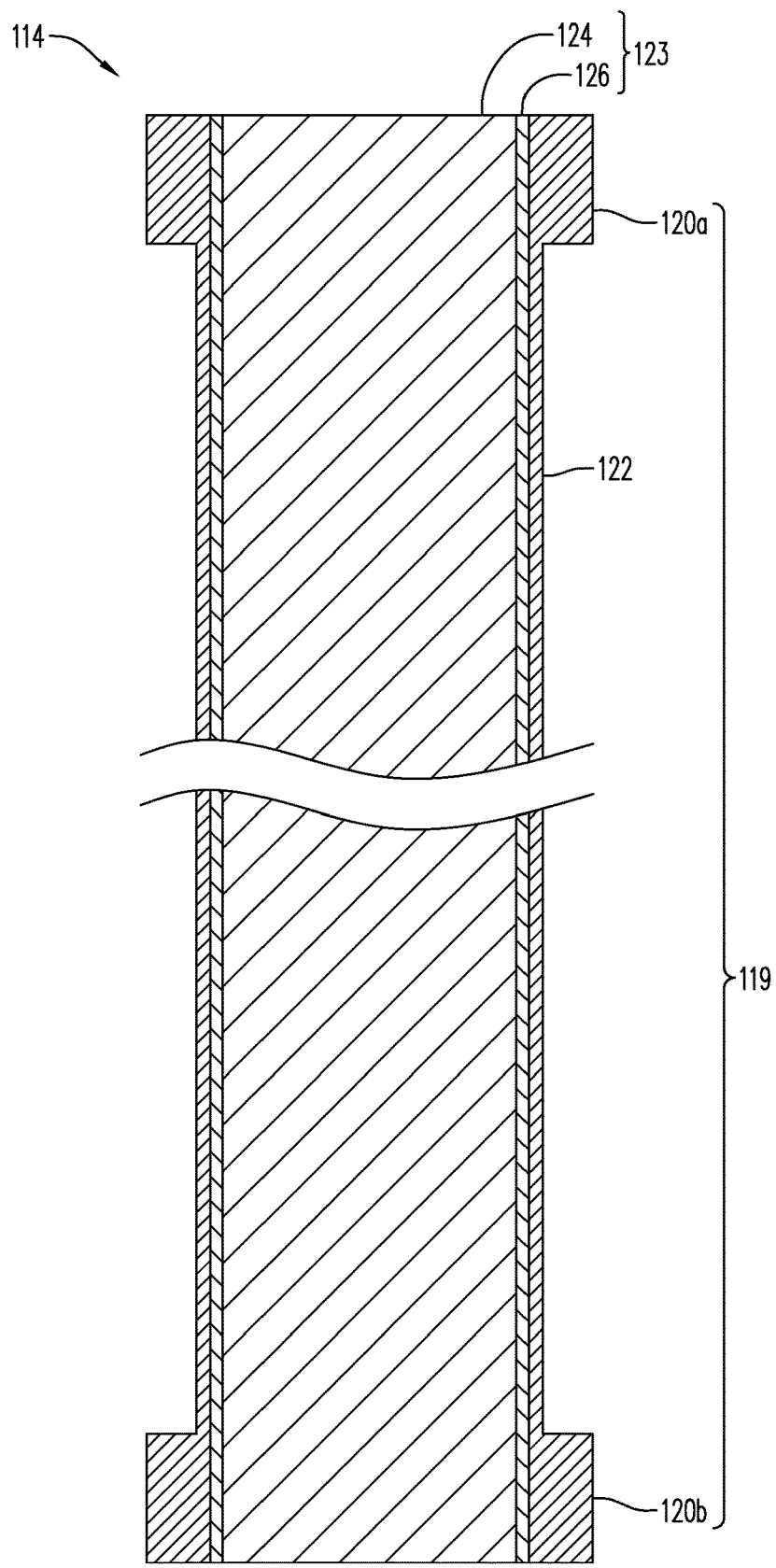
FIG. 1B is a cross-sectional view of the heater structure of FIG. 1A.

The recessed portion 122 of the shell layer 119 in FIGS. 1A-1B may have a resistivity of about 0.02 to 0.2 μΩ·m (e.g., about 0.08 to 0.14 μΩ·m or about 0.1 μΩ·m). Additionally, the recessed portion 122 of the shell layer 119 may have a resistance of about 1 to 10Ω (e.g., about 3 to 8Ω). As a result, when a current flows through the shell layer 119 from the first unrecessed portion 120a to the second unrecessed portion 120b (or vice versa), heat will be generated in the recessed portion 122 due to the higher resistance in the thinner recessed portion 122 relative to the thicker first unrecessed portion 120a and second unrecessed portion 120b of the shell layer 119. Accordingly, the pre-vapor formulation will be vaporized by the recessed portion 122 (rather than the first and second unrecessed portions 120a and 120b) of the shell layer 119.

The base wire 123 is insulated from the shell layer 119. As a result, the loss of the supplied current from the shell layer 119 and the dissipation of the generated heat from the recessed portion 122 thereof to the base wire 123 can be reduced or prevented. To achieve the pertinent insulation from the shell layer 119, the base wire 123 may be an anodized wire. In an example embodiment, the anodized wire is an object wire 124 coated with an anodic layer 126 (e.g., oxide layer). The object wire 124 may have a diameter of up to about 400 μm (e.g., about 100-400 μm). Also, the object wire 124 may be an aluminum wire, a titanium wire, a zinc wire, a magnesium wire, a niobium wire, a zirconium wire, a hafnium wire, or a tantalum wire. However, it should be understood that the object wire 124 may be formed of other suitable metals that are capable of being anodized to grow the anodic layer 126 thereon. The anodic layer 126 has a thickness of at least 500 nm (e.g., at least 1000 nm). Additionally, the anodic layer 126 may have a thickness of up to 10,000 nm. In furtherance of the reduction or prevention of the above-mentioned loss of the supplied current from the shell layer 119 and the dissipation of the generated heat from the recessed portion 122 thereof to the base wire 123, the anodic layer 126 may be grown so as to have a dielectric strength of at least 150 V.

Alternatively, to achieve the pertinent insulation from the shell layer 119, the base wire 123 may be a transition metal-based wire (e.g., 124) coated with vitreous enamel (e.g., 126). The transition metal-based wire may be a nickel wire, a nickel-chromium wire, or a stainless steel wire, although example embodiments are not limited thereto.

It should be understood that the heater structure 114 may be implemented in a variety of shapes, sizes, and forms. For instance, in an e-vapor device, the heater structure 114 may be loop-shaped, ring-shaped, or C-shaped to allow the use of a wick that is in elongated form (e.g., cord). In such an example, the wick would extend through the loop-shaped, ring-shaped, or C-shaped heater structure while also arranged in fluidic communication with the reservoir. Additionally, the wick may be thicker than those in the related art, thereby reducing or preventing the likelihood of clogging. Furthermore, the stronger and more robust nature of the heater structure 114 allows this structure to squeeze the wick to a greater degree than possible with other related heaters in the art.

Alternatively, the heater structure 114 may be arranged so as to apply a spring force against the dispensing interface of the pre-vapor sector. The dispensing interface may include a wick that is in planar form (e.g., pad) and in fluidic communication with the reservoir. In such an example, the heater structure 114 (e.g., recessed portion 122 of the shell layer 119) would press against the dispensing interface of the pre-vapor sector. For instance, the heater structure 114 may have a yield strength of about 50 to 600 MPa to allow the desired amount of pressure to be applied to the dispensing interface. The base wire 123 may be primarily responsible for the yield strength of the heater structure 114. Furthermore, to increase the contact area with the dispensing interface, the heater structure 114 may be provided with a winding pattern.

A method of generating a vapor for an e-vapor device may include thermally contacting a pre-vapor sector within the e-vapor device with a heater structure. The pre-vapor sector includes a reservoir and a dispensing interface. The dispensing interface may be in a form of an absorbent material that is arranged in fluidic communication with the reservoir and the heater structure. In particular, the pre-vapor formulation within the pre-vapor sector may directly contact the heater structure. The heater structure includes a base wire and a shell layer coating the base wire. The base wire is insulated from the shell layer. In an example embodiment, the base wire is electrically insulated (but not thermally insulated) from the shell layer. The shell layer includes a recessed portion between a first unrecessed portion and a second unrecessed portion. The thermally contacting step may include heating the pre-vapor formulation of the pre-vapor sector with the recessed portion of the shell layer to generate the vapor.

FIG. 1B is a cross-sectional view of the heater structure of FIG. 1A. Referring to FIG. 1B, the object wire 124 is electrically isolated from the shell layer 119 by the anodic layer 126. As a result, even when the object wire 124 and the shell layer 119 are conductors, the loss of current from the shell layer 119 to the object wire 124 can be mitigated or precluded by the anodic layer 126. Additionally, although the heater structure 114 in FIGS. 1A-1B appears as a stout, cylindrical structure (by virtue of the partial view thereof), it should be understood that the heater structure 114 can be relatively long and the underlying base wire 123 can be deformed to provide various foundational shapes and forms for the shell layer 119 to coat. In an example embodiment, the length of the recessed portion 122 (e.g., 20 mm) may be longer than a combined length of the first and second unrecessed portions 120a and 120b (e.g., 2 mm each) by about be five times or more. Furthermore, a majority (e.g., 90% or more) of the mass of the shell layer 119 may be in the first and second unrecessed portions 120a and 120b.

Figure 2A:
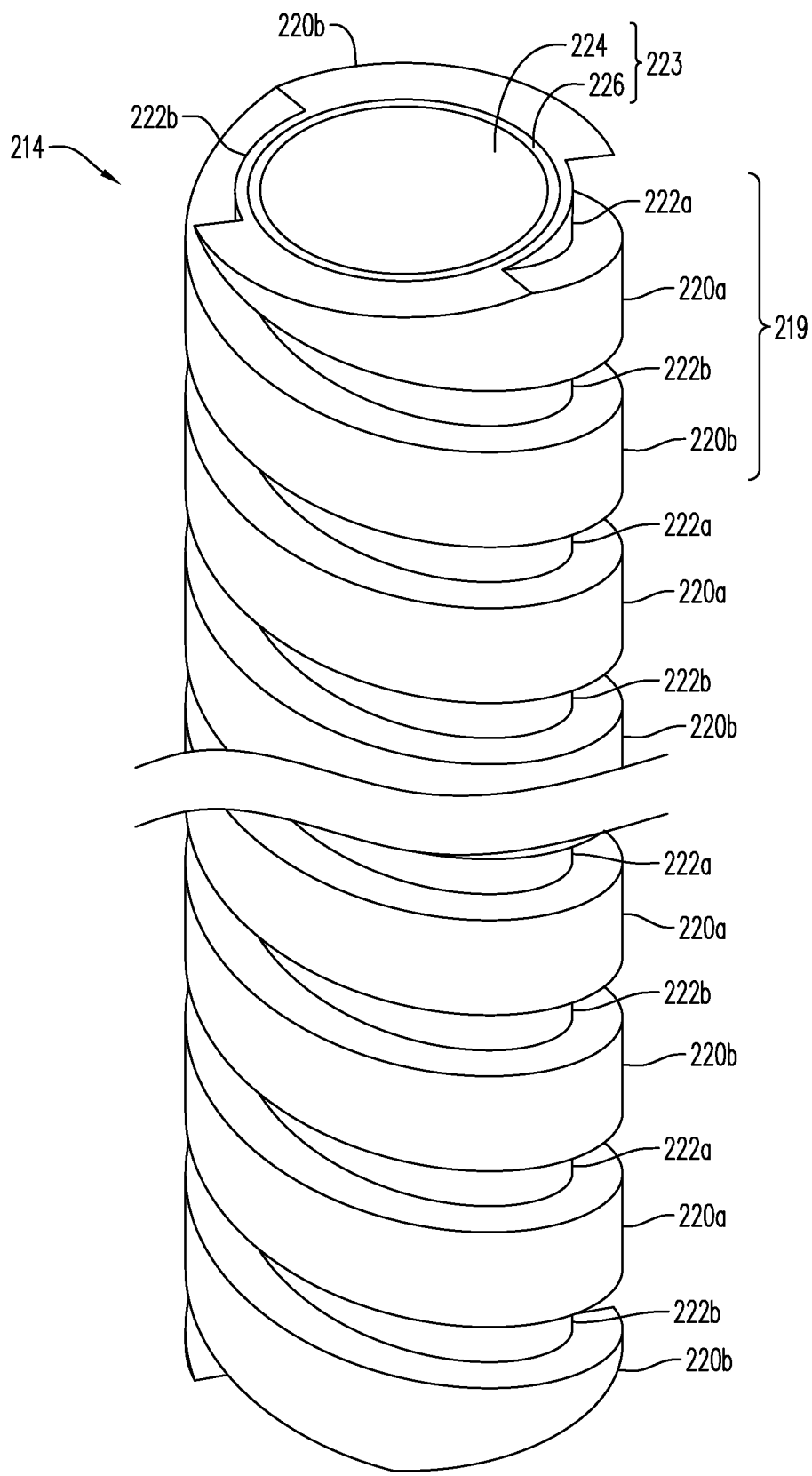
FIG. 2A is a partial, perspective view of a heater structure having a shell layer with a first recessed portion and a second recessed portion according to an example embodiment.

FIG. 2A is a partial, perspective view of a heater structure having a shell layer with a first recessed portion and a second recessed portion according to an example embodiment. Referring to FIG. 2A, the heater structure 214 includes a base wire 223 and a shell layer 219 coating the base wire 223. The base wire 223 may be an anodized wire. In an example embodiment, the anodized wire is an object wire 224 coated with an anodic layer 226. The object wire 224 may be insulated from the shell layer 219 by the anodic layer 226. The base wire 223 corresponds to the base wire 123 of FIGS. 1A-1B. Furthermore, the above-discussed aspects and considerations in connection with the shell layer 119 of FIGS. 1A-1B may also apply to the shell layer 219.

The shell layer 219 includes a first recessed portion 222a and a second recessed portion 222b. The first and second recessed portions 222a and 222b may originate from opposite surfaces of the shell layer 219 and coil around the base wire 223 so as to form alternately-arranged spiral grooves (e.g., double helix arrangement). As a result, first unrecessed portion 220a and the second unrecessed portion 220b are separated from each other by the first recessed portion 222a and the second recessed portion 222b. In particular, the first and second recessed portions 222a and 222b are between opposite sides of the first and second unrecessed portions 220a and 220b. Although FIG. 2A shows a relatively close-coiled arrangement for the heater structure 214, it should be understood that the arrangement may be more open such that the size of the recessed portions is increased so as to decrease the number of coils thereof.

To operate the heater structure 214, the first unrecessed portion 220a and the second unrecessed portion 220b of the shell layer 219 are connected to opposite terminals of a power source (e.g., battery). When a current flows from the first unrecessed portion 220a to the second unrecessed portion 220b (or vice versa), the first and second recessed portions 222a and 222b therebetween undergo resistive heating to facilitate the generation of a vapor. In an example embodiment, one or more wicks may be arranged in fluidic communication with the pre-vapor sector and also wrapped around the heater structure 214 so as to seat within the first recessed portion 222a and/or the second recessed portions 222b. In such an embodiment, the size of the first recessed portion 222a and the second recessed portions 222b can be modified as needed to accommodate the one or more wicks (or vice versa). The wick may also be in a form of a strip of an absorbent material to facilitate its positioning within the first recessed portion 222a and/or the second recessed portions 222b. Furthermore, one of the ends of the heater structure 214 may be angled so as to form a puncture device that is designed to pierce a container (e.g., capsule) of a pre-vapor formulation and, thus, place one or more wicks in fluidic communication with the pre-vapor formulation.

Figure 2B:
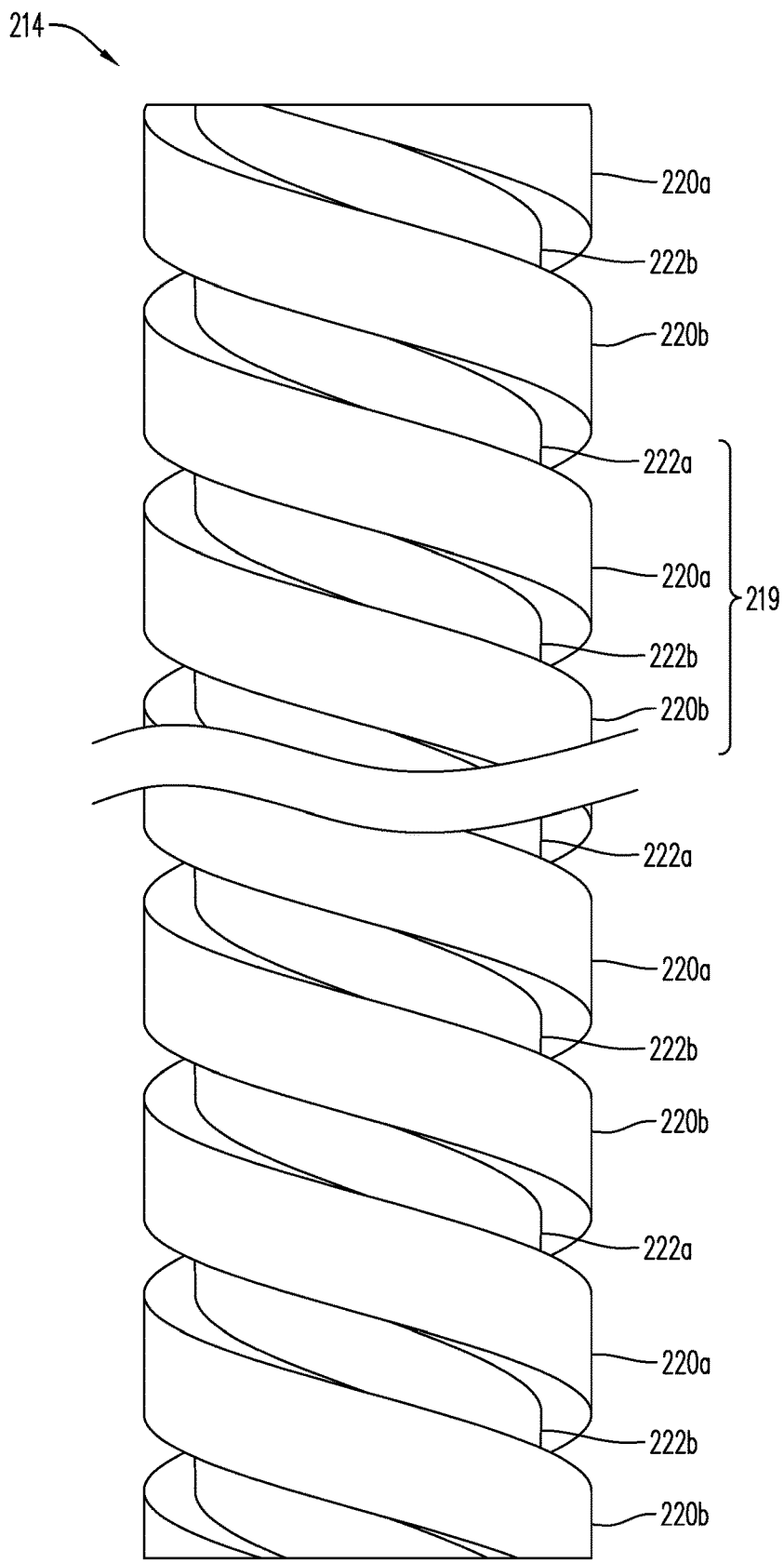
FIG. 2B is a side view of the heater structure of FIG. 2A.
Figure 2C:
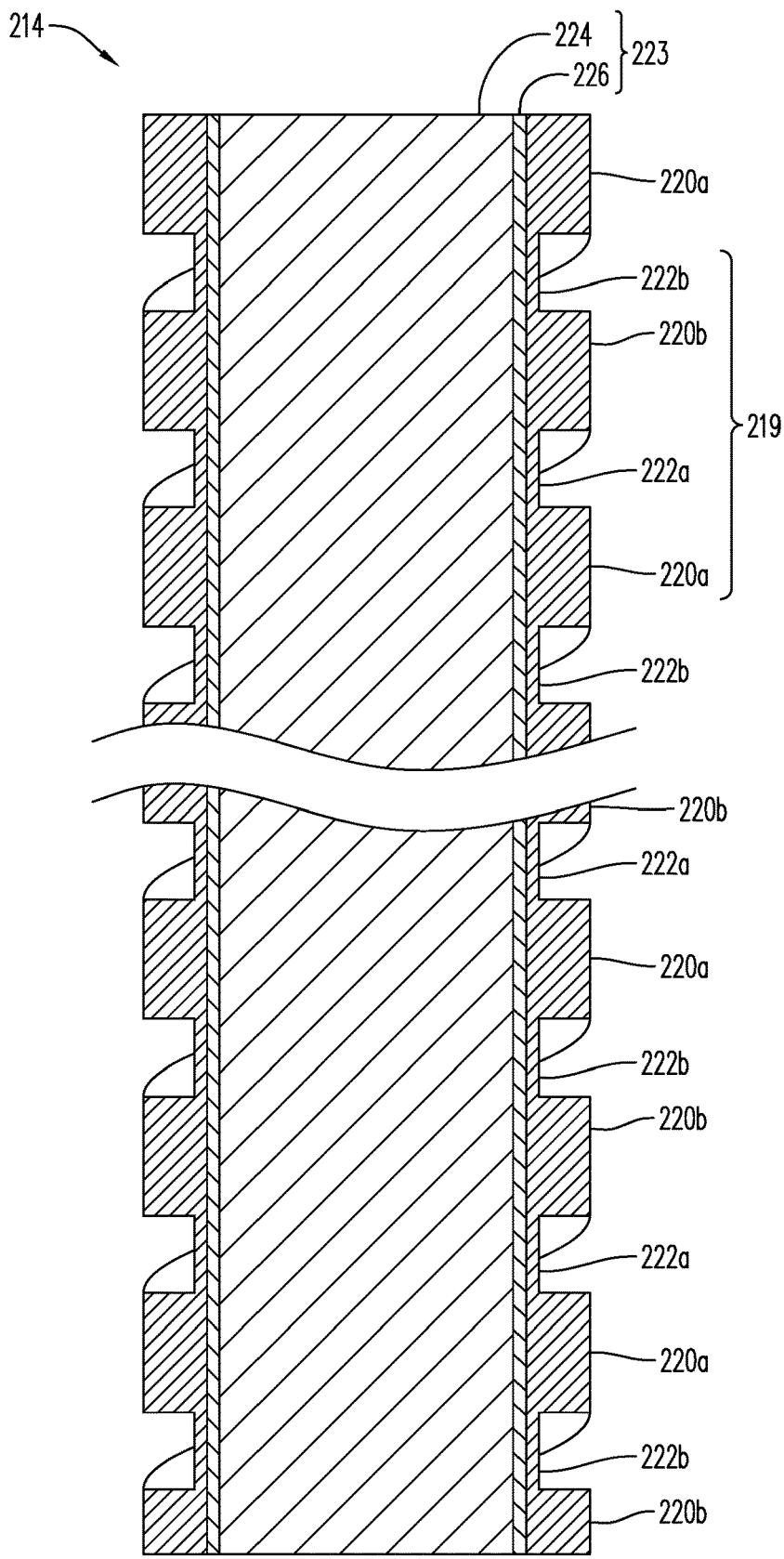
FIG. 2C is a cross-sectional view of the heater structure of FIG. 2A.

FIG. 2B is a side view of the heater structure of FIG. 2A. FIG. 2C is a cross-sectional view of the heater structure of FIG. 2A. Referring to FIGS. 2B-2C, the unrecessed portions alternate between the first and second unrecessed portions 220a and 220b along the length of the heater structure 214. Similarly, the recessed portions alternate between the first and second recessed portions 222a and 222b along the length of the heater structure 214.

Figure 3:
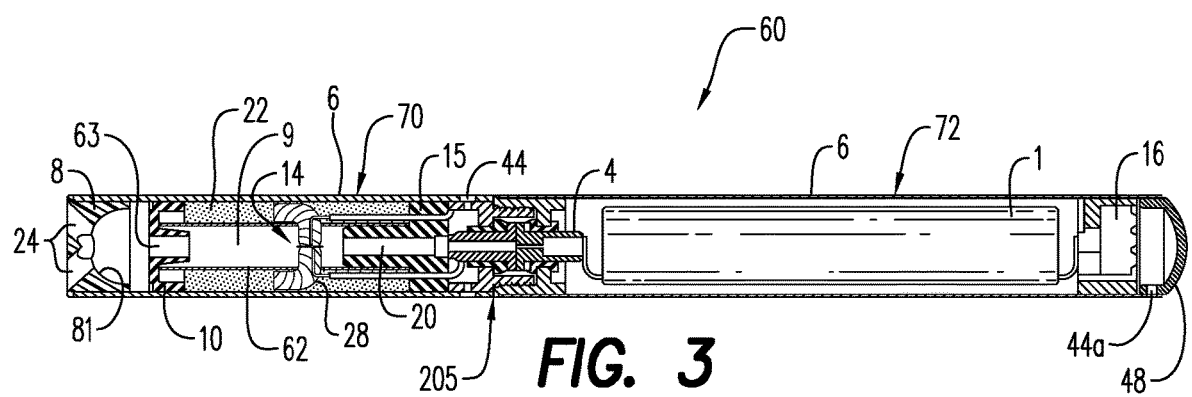
FIG. 3 is a cross-sectional view of an e-vapor device including a heater structure according to an example embodiment.

FIG. 3 is a cross-sectional view of an e-vapor device including a heater structure according to an example embodiment. Referring to FIG. 3, an e-vapor device 60 includes a first section 70 coupled to a second section 72 via a threaded connection 205. The first section 70 may be a replaceable cartridge, and the second section 72 may be a reusable fixture, although example embodiments are not limited thereto. The threaded connection 205 may be a combination of a male threaded member on the first section 70 and a female threaded receiver on the second section 72 (or vice versa). Alternatively, the threaded connection 205 may be in a form of other suitable structures, such as a snug-fit, detent, clamp, and/or clasp arrangement. The first section 70 includes an outer tube 6 (or housing) extending in a longitudinal direction and an inner tube 62 within the outer tube 6. The inner tube 62 may be coaxially positioned within the outer tube 6. The second section 72 may also include the outer tube 6 (or housing) extending in a longitudinal direction. In an alternative embodiment, the outer tube 6 can be a single tube housing both the first section 70 and the second section 72, and the entire e-vapor device 60 can be disposable.

The e-vapor device 60 includes a central air passage 20 defined in part by the inner tube 62 and an upstream seal 15. Additionally, the e-vapor device 60 includes a reservoir 22. The reservoir 22 is configured to hold a pre-vapor formulation and optionally a storage medium operable to store the pre-vapor formulation therein. In an example embodiment, the reservoir 22 is contained in an outer annulus between the outer tube 6 and the inner tube 62. The outer annulus is sealed by the seal 15 at an upstream end and by a stopper 10 at a downstream end so as to prevent leakage of the pre-vapor formulation from the reservoir 22.

A heater structure 14 is contained in the inner tube 62 downstream of and in a spaced apart relation to the portion of central air passage 20 defined by the seal 15. The heater structure 14 may be as described in connection with the heater structure 114 in FIGS. 1A-1B and can be in the form of a loop, although example embodiments are not limited thereto. A wick 28 is in communication with the pre-vapor formulation in the reservoir 22 and in communication with the heater structure 14 such that the wick 28 dispenses the pre-vapor formulation in proximate relation to the heater structure 14. Thus, the wick 28 may be regarded as a dispensing interface for the pre-vapor formulation. The combination of at least the reservoir 22 and the dispensing interface (e.g., wick 28) may be regarded as the pre-vapor sector.

The wick 28 may be constructed of a fibrous and flexible material. In particular, the wick 28 may include at least one filament having a capacity to draw a pre-vapor formulation into the wick 28. For example, the wick 28 may include a bundle of filaments, such as glass (or ceramic) filaments. In another instance, the wick 28 may include a bundle comprising a group of windings of glass filaments (e.g., three of such windings), all which arrangements are capable of drawing a pre-vapor formulation into the wick 28 via capillary action as a result of the interstitial spacing between the filaments. A power supply 1 in the second section 72 is operably connected to the heater structure 14 to apply a voltage across the heater structure 14. The e-vapor device 60 also includes at least one air inlet 44 operable to deliver air to the central air passage 20 and/or other portions of the inner tube 62.

The e-vapor device 60 further includes a mouth-end insert 8 having at least two off-axis, diverging outlets 24. The mouth-end insert 8 is in fluidic communication with the central air passage 20 via the interior of inner tube 62 and a central passage 63, which extends through the stopper 10. The heater structure 14 is configured to heat the pre-vapor formulation to a temperature sufficient to vaporize the pre-vapor formulation and form a vapor. Other orientations of the heater structure 14 (other than that shown in the drawings) are contemplated. For instance, although the heater structure 14 is shown as being arranged centrally within the inner tube 62, it should be understood that the heater structure 14 can also be arranged adjacent to an inner surface of the inner tube 62.

The wick 28, reservoir 22, and mouth-end insert 8 are contained in the first section 70, and the power supply 1 is contained in the second section 72. In an example embodiment, the first section (e.g., cartridge) 70 is disposable, and the second section (e.g., fixture) 72 is reusable. The first section 70 and second section 72 can be attached by a threaded connection 205, whereby the first section 70 can be replaced when the pre-vapor formulation in the reservoir 22 is depleted. Having a separate first section 70 and second section 72 provides a number of advantages. First, if the first section 70 contains the heater structure 14, the reservoir 22, and the wick 28, all elements which are potentially in contact with the pre-vapor formulation are disposed of when the first section 70 is replaced. Thus, there will be no cross-contamination between different mouth-end inserts 8 (e.g., when using different pre-vapor formulations). Also, if the first section 70 is replaced at suitable intervals, there is less chance of the heater structure 14 becoming clogged with the pre-vapor formulation. Optionally, the first section 70 and the second section 72 may be arranged to releaseably lock together when engaged.

Although not shown, the outer tube 6 can include a clear (transparent) window formed of a transparent material so as to allow an adult vaper to see the amount of pre-vapor formulation remaining in the reservoir 22. The clear window can extend at least a portion of the length of the first section 70 and can extend fully or partially about the circumference of the first section 70. In another example embodiment, the outer tube 6 can be at least partially formed of a transparent material so as to allow an adult vaper to see the amount of pre-vapor formulation remaining in the reservoir 22.

The at least one air inlet 44 may include one, two, three, four, five, or more air inlets. If there is more than one air inlet, the air inlets may be located at different locations along the e-vapor device 60. For example, an air inlet 44a can be positioned at the upstream end of the e-vapor device 60 adjacent a puff sensor 16 such that the puff sensor 16 facilitates the supply of power to the heater structure 14 upon sensing a negative pressure applied by the adult vaper. The air inlet 44a is in communication with the mouth-end insert 8 such that a draw upon the mouth-end insert 8 will activate the puff sensor 16. During a draw by an adult vaper, the air from the air inlet 44a will flow along the power supply 1 (e.g., battery) to the central air passage 20 in the seal 15 and/or to other portions of the inner tube 62 and/or outer tube 6. The at least one air inlet can be located adjacent to and upstream of the seal 15 or at any other desirable location. Altering the size and number of air inlets can also aid in establishing the desired resistance to draw (RTD) of the e-vapor device 60.

The heater structure 14 is arranged to communicate with the wick 28 and to heat the pre-vapor formulation contained in the wick 28 to a temperature sufficient to vaporize the pre-vapor formulation and form a vapor. The heater structure 14 may be a loop-type arrangement surrounding the wick 28. Examples of suitable electrically resistive materials for the heater structure 14 include titanium, zirconium, tantalum, and metals from the platinum group. Examples of suitable metal alloys include stainless steel, nickel-, cobalt-, chromium-, aluminum-, titanium-, zirconium-, hafnium-, niobium-, molybdenum-, tantalum-, tungsten-, tin-, gallium-, manganese-, and iron-containing alloys, and super-alloys based on nickel, iron, cobalt, and stainless steel. For instance, the heater structure 14 may include nickel aluminides, a material with a layer of alumina on the surface, iron aluminides, and other composite materials. The electrically resistive material may optionally be embedded in, encapsulated, or coated with an insulating material or vice-versa, depending on the kinetics of energy transfer and the external physicochemical properties required. In a non-limiting embodiment, the heater structure 14 comprises at least one material selected from the group consisting of stainless steel, copper, copper alloys, nickel-chromium alloys, superalloys, and combinations thereof. In another non-limiting embodiment, the heater structure 14 includes nickel-chromium alloys or iron-chromium alloys. Furthermore, the heater structure 14 can include a ceramic portion having an electrically resistive layer on an outside surface thereof. A higher resistivity for the heater structure 14 lowers the current draw or load on the power supply (battery) 1.

The heater structure 14 may heat the pre-vapor formulation in the wick 28 by thermal conduction. Alternatively, the heat from the heater structure 14 may be conducted to the pre-vapor formulation by means of a heat conductive element or the heater structure 14 may transfer the heat to the incoming ambient air that is drawn through the e-vapor device 60 during use, which in turn heats the pre-vapor formulation by convection.

The wick 28 extends through opposing openings in the inner tube 62 such that the end portions 31 of the wick 28 are in contact with the pre-vapor formulation in the reservoir 22. The filaments of the wick 28 may be generally aligned in a direction transverse to the longitudinal direction of the e-vapor device 60, although example embodiments are not limited thereto. During the operation of the e-vapor device 60, the wick 28 draws the pre-vapor formulation from the reservoir 22 to the heater structure 14 via capillary action as a result of the interstitial spacing between the filaments of the wick 28. The wick 28 can include filaments having a cross-section which is generally cross-shaped, clover-shaped, Y-shaped, or in any other suitable shape. The capillary properties of the wick 28, combined with the properties of the pre-vapor formulation, can be tailored to ensure that the wick 28 will be wet in the area of the heater structure 14 to avoid overheating. The wick 28 and the optional fibrous storage medium (of the reservoir 22) may be constructed from an alumina ceramic. Alternatively, the wick 28 may include glass fibers, and the optional fibrous storage medium may include a cellulosic material or polyethylene terephthalate.

The power supply 1 may include a battery arranged in the e-vapor device 60 such that the anode is downstream from the cathode. A battery anode connector 4 contacts the downstream end of the battery. The heater structure 14 is connected to the battery by two spaced apart electrical leads. The connection between the end portions 27 and 27' of the heater structure 14 and the electrical leads are highly conductive and temperature resistant, while the heater structure 14 is highly resistive so that heat generation occurs primarily along the heater structure 14 and not at the contacts.

The battery may be a Lithium-ion battery or one of its variants (e.g., a Lithium-ion polymer battery). The battery may also be a Nickel-metal hydride battery, a Nickel cadmium battery, a Lithium-manganese battery, a Lithium-cobalt battery, or a fuel cell. The e-vapor device 60 is usable until the energy in the power supply 1 is depleted, after which the power supply 1 will need to be replaced. Alternatively, the power supply 1 may be rechargeable and include circuitry allowing the battery to be chargeable by an external charging device. In this rechargeable embodiment, the circuitry, when charged, provides power for a desired or pre-determined number of applications of negative pressure, after which the circuitry must be re-connected to an external charging device.

The e-vapor device 60 also includes control circuitry including the puff sensor 16. The puff sensor 16 is operable to sense an air pressure drop and to initiate the application of voltage from the power supply 1 to the heater structure 14. The control circuitry includes a heater activation light 48 operable to glow when the heater structure 14 is activated. The heater activation light 48 may include an LED and may be arranged at an upstream end of the e-vapor device 60 so that the heater activation light 48 takes on the appearance of a burning coal during the application of negative pressure. Alternatively, the heater activation light 48 can be arranged on the side of the e-vapor device 60 so as to be more visible to the adult vaper and/or to provide a desired aesthetic appeal. The heater activation light 48 may have various shapes, sizes, quantities, and configurations. For instance, the heater activation light 48 may have a circular, elliptical, or polygonal shape (for one or more such lights). In another instance, the heater activation light 48 may have a linear or annular form that is continuous or segmented. For example, the heater activation light may be provided as an elongated strip that extends along the body of the e-vapor device 60. In another example, the heater activation light 48 may be provided as a ring that extends around the body of the e-vapor device 60. The ring may be in the first section 70 or the second section 72 (e.g., adjacent to the upstream end). It should be understood that the heater activation light 48 can be arranged on the end(s) and/or the sides of the e-vapor device 60. Furthermore, the heater activation light 48 can be utilized for e-vapor system diagnostics. The heater activation light 48 can also be configured such that the adult vaper can activate and/or deactivate the heater activation light 48 for privacy, such that, if desired, the heater activation light 48 would not activate during vaping.

The control circuitry integrated with the puff sensor 16 may automatically supply power to the heater structure 14 in response to the puff sensor 16, for example, with a maximum, time-period limiter. Alternatively, the control circuitry may include a manually operable switch for an adult vaper to initiate vaping. The time-period of the electric current supply to the heater structure 14 may be pre-set depending on the amount of pre-vapor formulation desired to be vaporized. The control circuitry may be programmable for this purpose. The control circuitry may supply power to the heater structure 14 as long as the puff sensor 16 detects a pressure drop.

When activated, the heater structure 14 heats a portion of the wick 28 surrounded by the heater structure 14 for less than about 10 seconds (e.g., less than about 7 seconds). Thus, the power cycle (or maximum length for the continuous application of negative pressure) can range from about 2 seconds to about 10 seconds (e.g., about 3 seconds to about 9 seconds, about 4 seconds to about 8 seconds, or about 5 seconds to about 7 seconds).

The reservoir 22 may at least partially surround the central air passage 20, and the heater structure 14 and the wick 28 may extend between portions of the reservoir 22. The optional storage medium within the reservoir 22 may be a fibrous material including cotton, polyethylene, polyester, rayon, and combinations thereof. The fibers may have a diameter ranging in size from about 6 microns to about 15 microns (e.g., about 8 microns to about 12 microns or about 9 microns to about 11 microns). Also, the fibers may be sized to be irrespirable and can have a cross-section with a Y shape, cross shape, clover shape, or any other suitable shape. Instead of fibers, the optional storage medium may be a sintered, porous, or foamed material. Furthermore, it should be understood that the reservoir 22 may just be a filled tank lacking a fibrous storage medium.

The pre-vapor formulation has a boiling point suitable for use in the e-vapor device 60. If the boiling point is too high, the heater structure 14 may not be able to adequately vaporize the pre-vapor formulation in the wick 28. Conversely, if the boiling point is too low, the pre-vapor formulation may prematurely vaporize without the heater structure 14 even being activated.

The pre-vapor formulation may be a tobacco-containing material including volatile tobacco flavor compounds which are released from the pre-vapor formulation upon heating. The pre-vapor formulation may also be a tobacco flavor containing material or a nicotine-containing material. Alternatively, or in addition thereto, the pre-vapor formulation may include a non-tobacco material. For instance, the pre-vapor formulation may include water, solvents, active ingredients, ethanol, plant extracts, and natural or artificial flavors. The pre-vapor formulation may further include a vapor former. Examples of suitable vapor formers are glycerine, propylene glycol, etc.

During vaping, the pre-vapor formulation is transferred from the reservoir 22 to the proximity of the heater structure 14 by capillary action via the wick 28. The wick 28 has a first end portion and an opposite second end portion 31. The first end portion and the second end portion 31 extend into opposite sides of the reservoir 22 to contact the pre-vapor formulation contained therein. The heater structure 14 surrounds at least a portion of the wick 28 such that when the heater structure 14 is activated, the pre-vapor formulation in that portion (e.g., central portion) of the wick 28 is vaporized by the heater structure 14 to form a vapor.

The reservoir 22 may be configured to protect the pre-vapor formulation therein from oxygen so that the risk of degradation of the pre-vapor formulation is significantly reduced. Additionally, the outer tube 6 may be configured to protect the pre-vapor formulation from light so that the risk of degradation of the pre-vapor formulation is significantly reduced.

The mouth-end insert 8 include at least two diverging outlets 24 (e.g., 3, 4, 5, or more). The outlets 24 of the mouth-end insert 8 are located at the ends of off-axis passages and are angled outwardly in relation to the longitudinal direction of the e-vapor device 60. As used herein, the term "off-axis" denotes at an angle to the longitudinal direction of the e-vapor device. Also, the mouth-end insert (or flow guide) 8 may include outlets uniformly distributed around the mouth-end insert 8 so as to substantially uniformly distribute the vapor in an adult vaper's mouth during vaping. Thus, as the vapor passes into an adult vaper's mouth, the vapor moves in different directions so as to provide a full mouth feel as compared to e-vapor devices having an on-axis single orifice which directs the vapor to a single location in an adult vaper's mouth.

The outlets 24 and off-axis passages are arranged such that droplets of unvaporized pre-vapor formulation (carried in the vapor impact interior surfaces 81 at the mouth-end insert 8 and/or interior surfaces of the off-axis passages) are removed or broken apart. The outlets 24 of the mouth-end insert 8 are located at the ends of the off-axis passages and may be angled at 5 to 60 degrees with respect to the central axis of the outer tube 6 so as to remove droplets of unvaporized pre-vapor formulation and to more completely distribute the vapor throughout a mouth of an adult vaper during vaping. Each outlet 24 may have a diameter of about 0.015 inch to about 0.090 inch (e.g., about 0.020 inch to about 0.040 inch or about 0.028 inch to about 0.038 inch). The size of the outlets 24 and off-axis passages along with the number of outlets 24 can be selected to adjust, if desired, the resistance to draw (RTD) of the e-vapor device 60.

An interior surface 81 of the mouth-end insert 8 may be a generally domed surface. Alternatively, the interior surface 81 of the mouth-end insert 8 may be generally cylindrical or frustoconical with a planar end surface. The interior surface 81 may be substantially uniform over the surface thereof or symmetrical about the longitudinal axis of the mouth-end insert 8. However, the interior surface 81 can alternatively be irregular and/or have other shapes.

The mouth-end insert 8 may be integrally affixed within the outer tube 6 of the first section 70. The mouth-end insert 8 may be formed of a polymer selected from the group consisting of low density polyethylene, high density polyethylene, polypropylene, polyvinylchloride, polyetheretherketone (PEEK), and combinations thereof. The mouth-end insert 8 may also be colored if desired.

The e-vapor device 60 may also include an air flow diverter. The air flow diverter is operable to manage the air flow at or around the heater structure 14 so as to abate a tendency for drawn air to cool the heater structure 14, which could otherwise lead to diminished vapor output. In an example embodiment, an air flow diverter may include an impervious plug at a downstream end of the central air passage 20 in seal 15. The central air passage 20 is an axially extending central passage in seal 15 and inner tube 62. The seal 15 seals the upstream end of the annulus between the outer tube 6 and the inner tube 62. The air flow diverter may include at least one radial air channel to direct the air from the central air passage 20 outward towards the inner tube 62 and into an outer air passage 9 defined between an outer periphery of a downstream end portion of the seal 15 and the inner wall of inner tube 62.

The diameter of the bore of the central air passage 20 may be substantially the same as the diameter of the at least one radial air channel. The diameter of the bore of the central air passage 20 and the at least one radial air channel may range from about 1.5 mm to about 3.5 mm (e.g., about 2.0 mm to about 3.0 mm). Optionally, the diameter of the bore of the central air passage 20 and the at least one radial air channel can be adjusted to control the resistance to draw (RTD) of the e-vapor device 60. During vaping, the air flows into the bore of the central air passage 20, through the at least one radial air channel, and into the outer air passage 9 such that a lesser portion of the air flow is directed at a central portion of the heater structure 14 so as to reduce or minimize the cooling effect of the airflow on the heater structure 14 during the heating cycles. Thus, the incoming air is directed away from the center of the heater structure 14 and the air velocity past the heater structure 14 is reduced as compared to when the air flows through a central opening in the seal 15 oriented directly in line with a middle portion of the heater structure 14.

Figure 4:
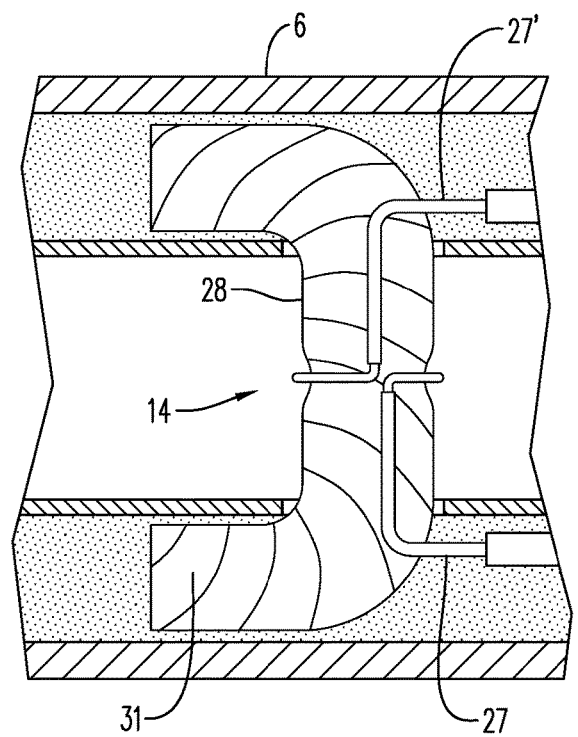
FIG. 4 is an enlarged view of the portion of the e-vapor device including the heater structure of FIG. 3.

FIG. 4 is an enlarged view of the portion of the e-vapor device including the heater structure of FIG. 3. Referring to FIGS. 3-4, the heater structure 14 is a loop-type arrangement with the wick 28 extending therethrough. The principle of heater structure 14 in FIGS. 3-4 may be as described in connection with the heater structure 114 in FIGS. 1A-1B. In particular, the base wire and shell layer of the heater structure 14 in FIGS. 3-4 correspond to the base wire 123 and shell layer 119 of the heater structure 114 in FIGS. 1A-1B, respectively. Notably, the base wire 123 in FIGS. 1A-1B is configured as a loop in FIGS. 3-4. Additionally, the shell layer 119 in FIGS. 1A-1B is coated around the loop in FIGS. 3-4. Furthermore, as shown in FIGS. 3-4, one unrecessed portion extends upward to connect to a positive (or negative) terminal of the power supply 1 via an electrical lead, while the opposing unrecessed portion extends downward to connect to a negative (or positive) terminal of the power supply 1 via another electrical lead.

As shown in FIGS. 3-4, the wick 28 extends through the opening of the loop-type arrangement of the heater structure 14. The end portions 31 of the wick 28 also extend through the inner tube 62 so as to be in fluidic communication with the pre-vapor formulation in the reservoir 22. As a result, when a current is supplied to the heater structure 14 from the power supply 1, the recessed portions of the shell layer will undergo resistive heating and vaporize the pre-vapor formulation in the wick 28 to produce a vapor that is drawn through an outlet of the device when a negative pressure is applied. Alternatively, it should be understood that the heater structure 214 of FIGS. 2A-2B may also be used in the e-vapor device 60.

Figure 5:
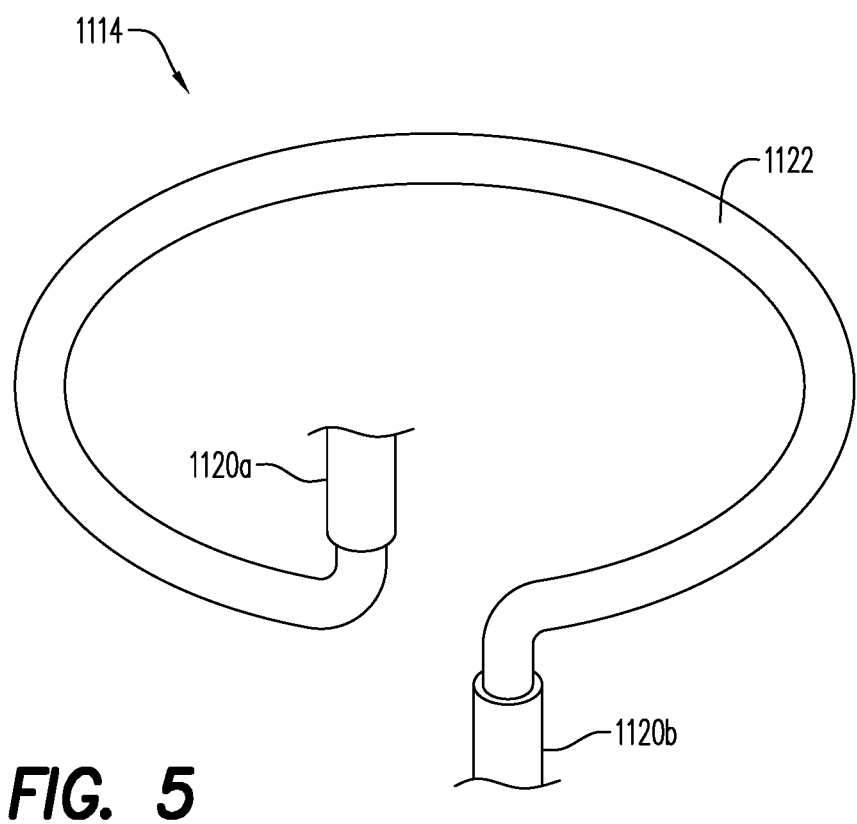
FIG. 5 is a perspective view of a heater structure having a loop shape and unrecessed portions extending in opposite directions according to an example embodiment.

FIG. 5 is a perspective view of a heater structure having a loop shape and unrecessed portions extending in opposite directions according to an example embodiment. Referring to FIG. 5, the heater structure 1114 may correspond to the heater structure 14 in FIGS. 3-4. Additionally, the first unrecessed portion 1120a, the recessed portion 1122, and the second unrecessed portion 1120b of FIG. 5 may correspond to the first unrecessed portion 120a, the recessed portion 122, and the second unrecessed portion 120b of FIGS. 1A-1B. The opening defined by the recessed portion 1122 is intended to receive a wick having an elongated form.

Although not shown in FIG. 5, the first unrecessed portion 1120a and the second unrecessed portion 1120b will be connected to a power supply (e.g., via electrical leads). Additionally, it should be understood that the first unrecessed portion 1120a and the second unrecessed portion 1120b may be oriented in various directions based on the location of the electrical leads (e.g., both up, both down). Furthermore, the recessed portion 1122 may be ring-shaped or oval-shaped based on a top or bottom view. When the recessed portion 1122 is ring-shaped, the inner diameter may be equal to or less than a diameter of the wick intended to extend therethrough. Alternatively, it should be understood that the heater structure 214 of FIGS. 2A-2B may also be applied to the non-limiting embodiment of FIG. 5.

Figure 6:
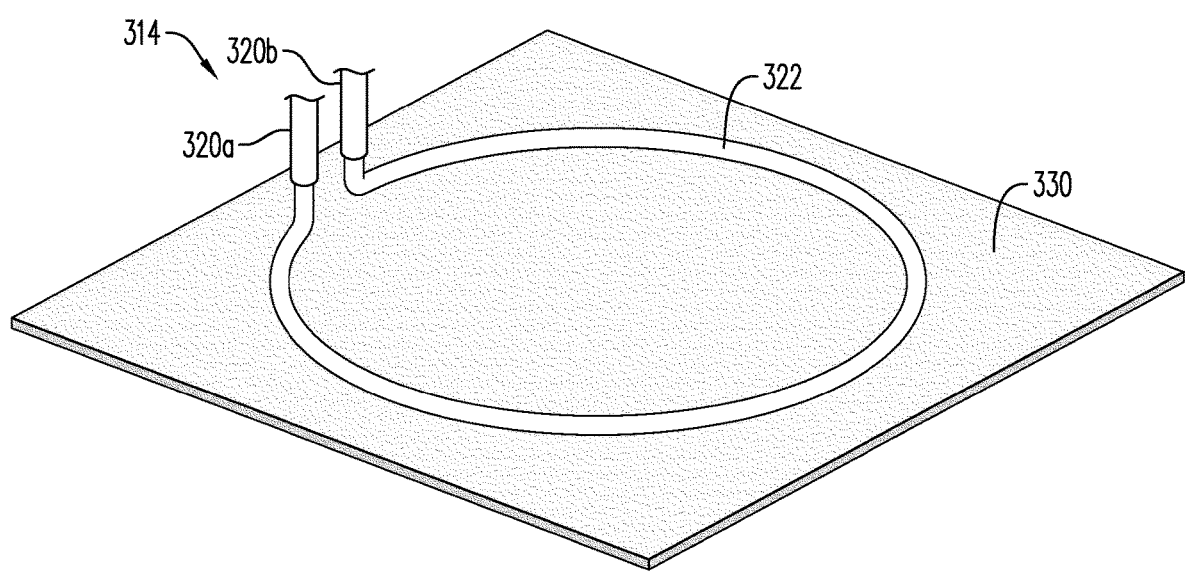
FIG. 6 is a perspective view of a heater structure having a loop shape and unrecessed portions extending in the same direction according to an example embodiment.

FIG. 6 is a perspective view of a heater structure having a loop shape and unrecessed portions extending in the same direction according to an example embodiment. Referring to FIG. 6, the heater structure 314 is configured to be pressed against a dispensing interface 330 of a pre-vapor sector of an e-vapor device. The first unrecessed portion 320a, the recessed portion 322, and the second unrecessed portion 320b of FIG. 6 may correspond to the first unrecessed portion 120a, the recessed portion 122, and the second unrecessed portion 120b of FIGS. 1A-1B. Although the recessed portion 322 is shown as being formed into a loop shape, it will be appreciated that the recessed portion 322 may be manipulated to continue to circle within itself to form a spiral shape, which will provide a greater contact area with the dispensing interface 330.

The dispensing interface 330 may be a wick having a planar form. In an e-vapor device, the dispensing interface 330 may be disposed in or around an opening (e.g., in inner tube 62) leading into the reservoir. The shape of the dispensing interface 330 and the heater structure 314 making contact therewith may correspond to the shape of the opening (e.g., in inner tube 62) leading into the reservoir. Thus, if the opening has a circular shape, then the dispensing interface 330 and the heater structure 314 may also have a circular shape. In addition, because the heater structure 314 can be configured to minimize the quantity of the recessed portion 322 that does not contact the dispensing interface 330 (e.g., via the first and second unrecessed portions 320a and 320b), the amount of wasted heat can be decreased.

The first unrecessed portion 320a and the second unrecessed portion 320b may function as a handle and/or as a mechanism for applying a spring force against the dispensing interface 330. For example, to apply a spring force against the dispensing interface 330, the first unrecessed portion 320a and the second unrecessed portion 320b may be curved or bent to allow the resilience of the underlying base wire to press the recessed portion 322 into the dispensing interface 330. Furthermore, although not shown in FIG. 6, the first unrecessed portion 320a and the second unrecessed portion 320b will be connected to a power supply (e.g., via electrical leads). During vaping, the heater structure 314 will vaporize the pre-vapor formulation in the dispensing interface 330 to form a vapor that is drawn through an outlet of the device when a negative pressure is applied. Alternatively, it should be understood that the heater structure 214 of FIGS. 2A-2B may also be applied to the non-limiting embodiment of FIG. 6.

Figure 7:
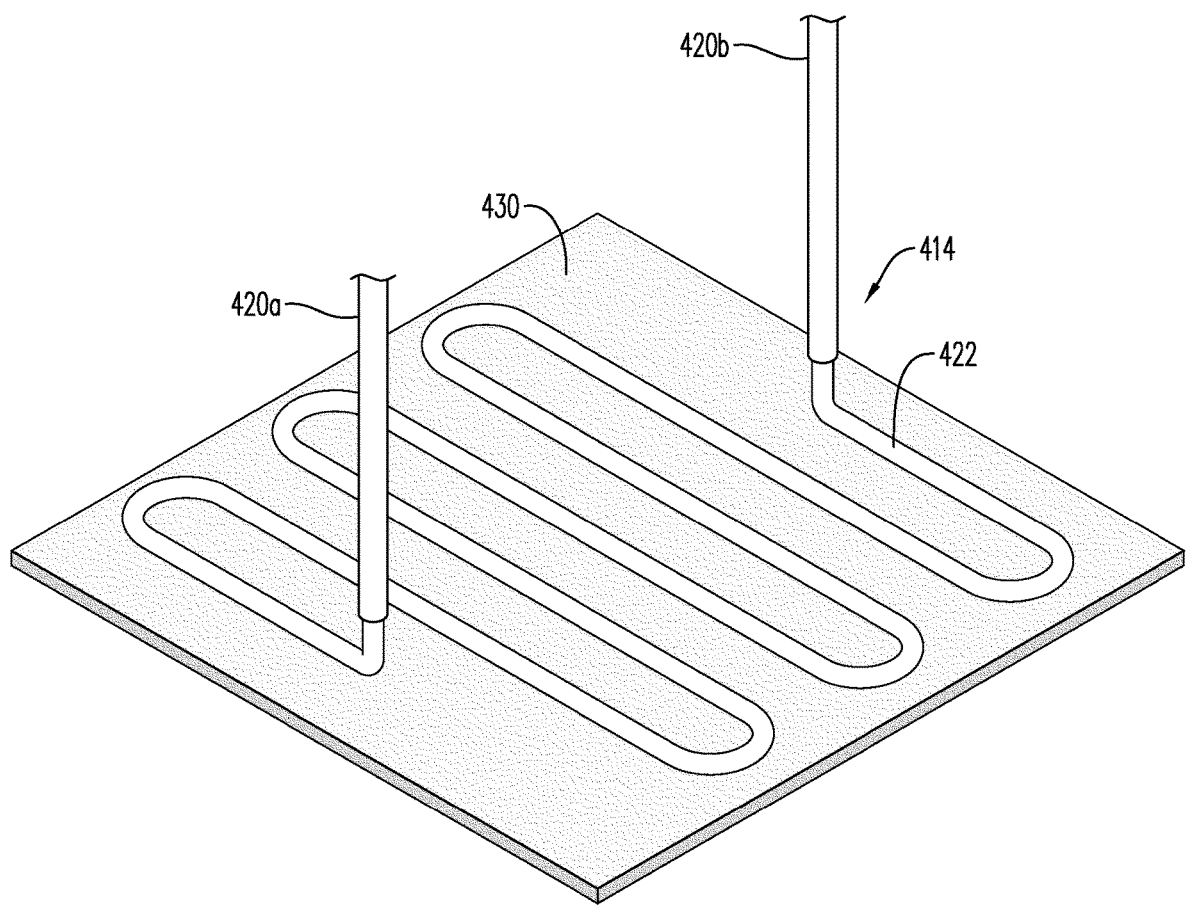
FIG. 7 is a perspective view of a heater structure having a winding form that resembles a polygonal shape according to an example embodiment.

FIG. 7 is a perspective view of a heater structure having a winding form that resembles a polygonal shape according to an example embodiment. Referring to FIG. 7, the heater structure 414 is configured to be pressed against a dispensing interface 430 of a pre-vapor sector of an e-vapor device. The first unrecessed portion 420a, the recessed portion 422, and the second unrecessed portion 420b of FIG. 7 may correspond to the first unrecessed portion 120a, the recessed portion 122, and the second unrecessed portion 120b of FIGS. 1A-1B. As shown in FIG. 7, the heater structure 414 has a winding form that resembles a polygonal shape (e.g., square, rectangle). The dispensing interface 430 may be a wick having a planar form. In an e-vapor device, the dispensing interface 430 may be disposed in or around an opening (e.g., in inner tube 62) leading into the reservoir. The first unrecessed portion 420a and the second unrecessed portion 420b may function as a handle and/or as a mechanism for applying a spring force against the dispensing interface 430. Furthermore, although not shown in FIG. 7, the first unrecessed portion 420a and the second unrecessed portion 420b will be connected to a power supply (e.g., via electrical leads). During vaping, the heater structure 414 will vaporize the pre-vapor formulation in the dispensing interface 430 to form a vapor that is drawn through an outlet of the device when a negative pressure is applied. Alternatively, it should be understood that the heater structure 214 of FIGS. 2A-2B may also be applied to the non-limiting embodiment of FIG. 7.

Figure 8:
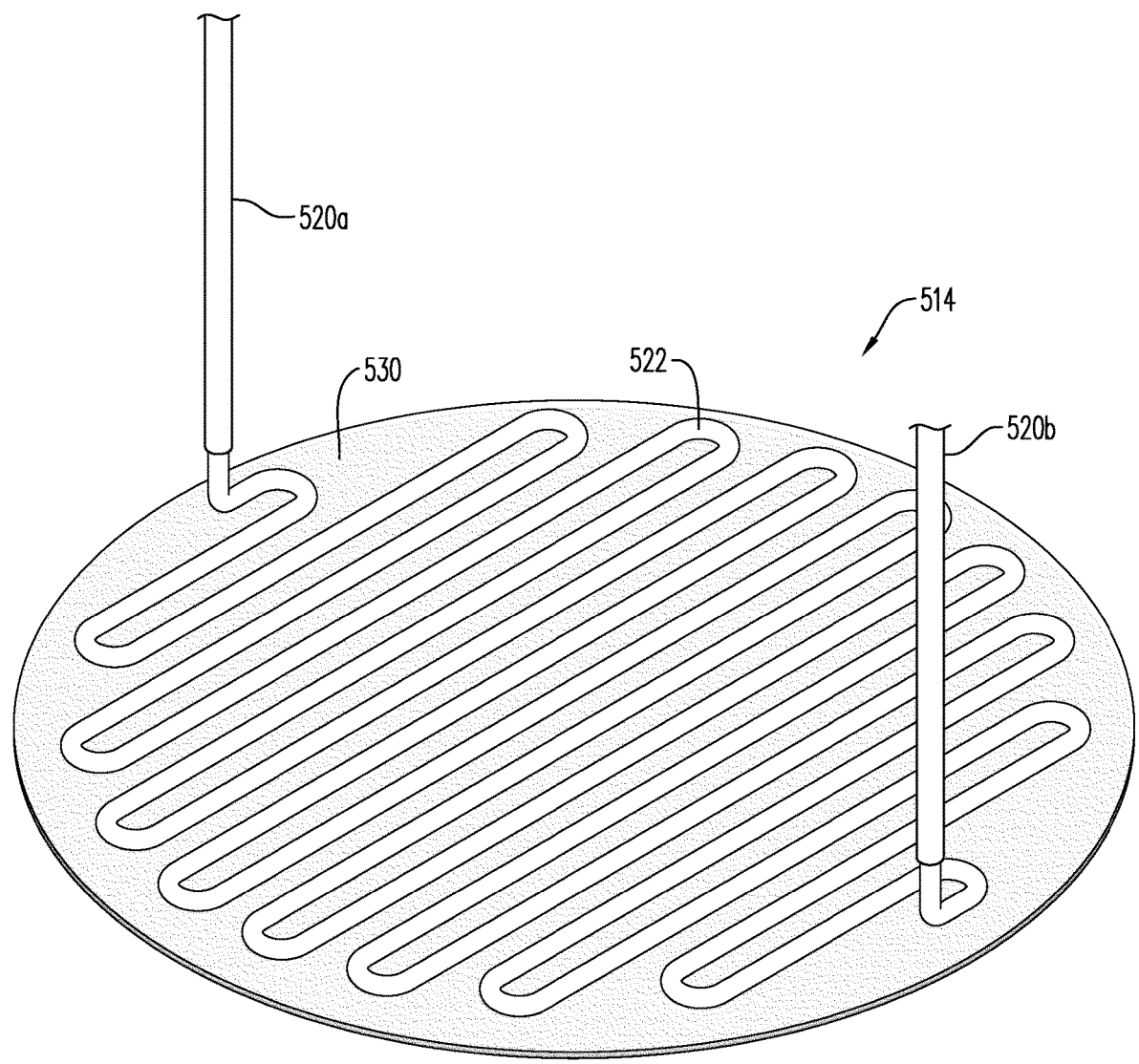
FIG. 8 is a perspective view of a heater structure having a winding form that resembles a circular shape according to an example embodiment.

FIG. 8 is a perspective view of a heater structure having a winding form that resembles a circular shape according to an example embodiment. Referring to FIG. 8, the heater structure 514 is configured to be pressed against a dispensing interface 530 of a pre-vapor sector of an e-vapor device. The first unrecessed portion 520a, the recessed portion 522, and the second unrecessed portion 520b of FIG. 8 may correspond to the first unrecessed portion 120a, the recessed portion 122, and the second unrecessed portion 120b of FIGS. 1A-1B. As shown in FIG. 8, the heater structure 514 has a winding form that resembles a circular shape. The dispensing interface 530 may be a wick having a planar form. In an e-vapor device, the dispensing interface 530 may be disposed in or around an opening (e.g., in inner tube 62) leading into the reservoir. The first unrecessed portion 520a and the second unrecessed portion 520b may function as a handle and/or as a mechanism for applying a spring force against the dispensing interface 530. Furthermore, although not shown in FIG. 8, the first unrecessed portion 520a and the second unrecessed portion 520b will be connected to a power supply (e.g., via electrical leads). During vaping, the heater structure 514 will vaporize the pre-vapor formulation in the dispensing interface 530 to form a vapor that is drawn through an outlet of the device when a negative pressure is applied. Alternatively, it should be understood that the heater structure 214 of FIGS. 2A-2B may also be applied to the non-limiting embodiment of FIG. 8.

In addition to the examples discussed herein, the heater structure may have a helical form that resembles a cylindrical shape (or even a conical shape). For instance, the base wire serves as a framework for the heater structure and may be a cylindrical helix with the shell layer coating the base wire. The heater structure may be arranged within an inner tube (e.g., inner tube 62) of an e-vapor device such that the free length of the helical form extends coaxially with the inner tube along a portion or an entirety thereof. Additionally, a dispensing interface (e.g., absorbent layer) may be disposed between the heater structure and the inner tube. One or more absorbent layers (e.g., gauze) serving as the dispensing interface may wrapped around the heater structure. In this non-limiting embodiment, the absorbent layer serving as the dispensing interface may be pressed against the interior surface of the inner tube via the resiliency of the heater structure. In this regard, the outer diameter of the helical form of the heater structure may correspond approximately to the inner diameter of the inner tube (or otherwise be appropriately sized to take into account the thickness of the dispensing interface) so as to exert a spring force that causes the absorbent layer serving as the dispensing interface to be pressed against the interior surface of the inner tube. Furthermore, the inner tube may also have one or more holes that allow pre-vapor formulation from the reservoir (e.g., reservoir 22) to be drawn into the dispensing interface via capillary action. As a result, when the e-vapor device is activated, the heater structure will vaporize the pre-vapor formulation in the dispensing interface to form a vapor that is drawn through an outlet of the device when a negative pressure is applied. In the configuration, the reservoir may optionally be in a form of a filled tank that does not include a storage medium (e.g., fibrous material).

While a number of example embodiments have been disclosed herein, it should be understood that other variations may be possible. Such variations are not to be regarded as a departure from the spirit and scope of the present disclosure, and all such modifications that would be appreciated by one ordinarily skilled in the art based on the teachings herein are intended to be included within the scope of the following claims.

The invention claimed is:

1. An e-vapor device, comprising:
a pre-vapor sector configured to hold and dispense a pre-vapor formulation; and
a heater structure arranged in thermal contact with the pre-vapor sector, the heater structure including a base wire and a shell layer coating the base wire, the base wire being insulated from the shell layer, the shell layer including at least one recessed portion between a first unrecessed portion and a second unrecessed portion, the at least one recessed portion being a thinner section of the shell layer that is configured to vaporize the pre-vapor formulation to generate a vapor, a thickness of the at least one recessed portion of the shell layer ranging from 0.01 to 1 μm.

2. The e-vapor device of claim 1, wherein the pre-vapor sector includes a reservoir and a dispensing interface.

3. The e-vapor device of claim 2, wherein the at least one recessed portion of the shell layer is arranged to press against the dispensing interface of the pre-vapor sector.

4. The e-vapor device of claim 1, wherein the heater structure has a yield strength ranging from 50 to 600 MPa.

5. The e-vapor device of claim 1, wherein
the base wire is an anodized wire.

6. The e-vapor device of claim 5, wherein the anodized wire is an object wire coated with an anodic layer.

7. The e-vapor device of claim 6, wherein the object wire is an aluminum wire, a titanium wire, a zinc wire, a magnesium wire, a niobium wire, a zirconium wire, a hafnium wire, or a tantalum wire.

8. The e-vapor device of claim 6, wherein the anodic layer has a dielectric strength of at least 150 V.

9. The e-vapor device of claim 6, wherein the anodic layer has a thickness ranging from 500 to 10,000 nm.

10. The e-vapor device of claim 1, wherein
the base wire is a transition metal-based wire coated with vitreous enamel.

11. The e-vapor device of claim 10, wherein the transition metal-based wire is a nickel wire, a nickel-chromium wire, or a stainless steel wire.

12. The e-vapor device of claim 1, wherein the first unrecessed portion is separated from the second unrecessed portion by the at least one recessed portion of the shell layer, the at least one recessed portion configured to reach a temperature that is at least double a temperature of the first and second unrecessed portions when a current flows through the shell layer.

13. The e-vapor device of claim 1, wherein a thickness of the first and second unrecessed portions of the shell layer ranges from 10 to 100 μm.

14. The e-vapor device of claim 1, wherein the first and second unrecessed portions of the shell layer are connected to opposite terminals of a power source.

15. The e-vapor device of claim 1, wherein the at least one recessed portion of the shell layer has a resistivity ranging from 0.02 to 0.2 μm.

16. The e-vapor device of claim 1, wherein the shell layer is formed of platinum or gold.

17. The e-vapor device of claim 1, wherein the at least one recessed portion is in a form of a first recessed portion and a second recessed portion, the first and second recessed portions being between opposite sides of the first and second unrecessed portions, the first and second recessed portions coiling around the base wire.

18. A method of generating a vapor for an e-vapor device, the method comprising:
thermally contacting a pre-vapor sector within the e-vapor device with a heater structure, the heater structure including a base wire and a shell layer coating the base wire, the base wire being insulated from the shell layer, the shell layer including at least one recessed portion between a first unrecessed portion and a second unrecessed portion, a thickness of the at least one recessed portion of the shell layer ranging from 0.01 to 1 μm.

19. The method of claim 18, wherein the thermally contacting includes heating a pre-vapor formulation of the pre-vapor sector with the at least one recessed portion of the shell layer to generate the vapor.

* * * * *